(12) United States Patent
Mast et al.

(10) Patent No.: US 8,702,908 B1
(45) Date of Patent: Apr. 22, 2014

(54) REDUCING PRODUCT VARIATIONS VIA VARIANCE PARTITION ANALYSIS

(71) Applicant: ABB Technology AG., Zurich (CH)

(72) Inventors: Timothy Andrew Mast, Plain City, OH (US); Kevin Dale Starr, Lancaster, OH (US)

(73) Assignee: ABB Technology AG, Zurich (CH)

( * ) Notice: Subject to any disclaimer, the term of this patent is extended or adjusted under 35 U.S.C. 154(b) by 0 days.

(21) Appl. No.: 13/751,198

(22) Filed: Jan. 28, 2013

(51) Int. Cl.
  *D21F 11/00* (2006.01)
(52) U.S. Cl.
  USPC ........... 162/198; 162/263; 700/127; 700/128; 700/129
(58) Field of Classification Search
  USPC ............ 162/198, 263; 700/127–129; 702/150
  See application file for complete search history.

(56) References Cited

U.S. PATENT DOCUMENTS

| | | | |
|---|---|---|---|
| 3,612,839 A | 10/1971 | DeWitt et al. | |
| 5,960,374 A | 9/1999 | Lausier | |
| 6,452,679 B1 | 9/2002 | Workman, Jr. | |
| 6,950,777 B1 * | 9/2005 | Lilburn et al. | 702/179 |
| 7,593,106 B2 * | 9/2009 | Hellstrom | 356/430 |
| 7,751,923 B2 | 7/2010 | Koenig et al. | |
| 8,155,932 B2 | 4/2012 | Berggren et al. | |
| 2008/0073050 A1 * | 3/2008 | Muench | 162/198 |
| 2010/0198364 A1 | 8/2010 | Chen et al. | |

FOREIGN PATENT DOCUMENTS

| | | |
|---|---|---|
| EP | 0765474 B1 | 10/2002 |
| WO | 2004101886 A2 | 11/2004 |
| WO | 2008041067 A2 | 4/2008 |

OTHER PUBLICATIONS

Nuyan et al., Unbiased Estimation of Variability from Scanning Measurements, 2010.*
TAPPI TIP-1101-01, Calculations and Partitioning of Variance Using Paper Machine Scanning Sensor Measurements, 1996.*
Leiviska et al. Fapet Oy, Book 14, Process Control, Chapter 8, 1999.*
Rudolf Munch, Variance Partition Analysis—Starting Point for Profile Optimization, 28 Sheets, downloaded Jan. 25, 2013, Voith Paper Automation GmbH, http//www.tappi.org/Downloads/Conference-Papers/2007/2007-PIMAPapermaker/07PAP85.aspx.
Shih-Chin Chen, Analysis of Sheet Variations—Insights of Two-Dimensional Variations, 2011, 13 sheets (pp. 990-1002, PaperCon 2011, http://www.tappi.org/Downloads/Conference-Papers/2011/2011-PaperCon-Conference/11PAP64.aspx.
Parisa Towfighi, Estimating Paper Sheet Process Variations for Scanned Data Using Compressive Sensing, Apr. 2011, 126 sheets, The University of British Columbia, http://circle.ubc.ca/bitstream/handle/2429/33950/ubc_2011_spring_towfighi_parisa.pdf?sequence=1.
Chris Rogers, Driving Pulp & Paper Performance Through Variation Reduction Part 1, Aug. 2011, pp. 9, Honeywell Process Solutions, https://www.honeywellprocess.com/library/marketing/whitepapers/honeywell-control-performance-monitor-pandpvariationreductionpart1-wp653.pdf.
Chris Rogers, Driving Pulp & Paper Performance Through Variation Reduction Part 2, Jun. 2011, pp. 9, Honeywell Process Solutions, https://www.honeywellprocess.com/library/marketing/whitepapers/honeywell-control-performance-monitor-pandpvariationreductionpart2-wp656.pdf.

* cited by examiner

*Primary Examiner* — Mark Halpern
(74) *Attorney, Agent, or Firm* — Driggs, Hogg, Daugherty & Del Zoppo Co., L.P.A.; Patrick J. Dougherty

(57) ABSTRACT

Normalized values are determined from variance partition analysis data boxes acquired for a reel of paper. The value include an average value of variability of machine direction long-term scan energy over a time period; an average value of variability of cross direction profile scan energy observed in a spatial domain over a second time period; an average value of variability of energy of a remainder of data points that are averaged out from a total of machine direction long-term scan average energy variability and cross direction profile scan average energy variability during a third time period; and a total variability value as a function of the machine direction long-term scan average energy variability, the cross direction profile scan average energy variability and the data points remainder average energy variability. An automated diagnosis and analysis function is performed that is specific to one of the values exceeding a threshold.

20 Claims, 7 Drawing Sheets

| Sensor | Cond. Weight | Moisture | Caliper | Ash | Size Moisture |
|---|---|---|---|---|---|
| Goal | < 1.5 | < 10.0 | < 1.0 | < 4.5 | < 10.0 |
| PM 1 | 1.4 | 17.1 | 0.9 | 5.1 | 25.1 |
| PM 2 | 2.6 | 9.4 | 2.0 | 4.1 | |
| PM 3 | 1.2 | 7.2 | | | |
| PM 4 | 2.5 | 15.1 | 0.8 | 5.5 | 15.7 |

| | Sensor | Cond. Weight | Moisture | Caliper | Ash | Size Moisture |
|---|---|---|---|---|---|---|
| PM 1 | MDS | 70 | 50.5 | 3.9 | 68.0 | 16.6 | 32.3 |
| | CD | 20 | 40.3 | 94.4 | 21.0 | 2.3 | 63.0 |
| | MDL | 10 | 6.4 | 0.8 | 11.0 | 64.0 | 3.7 |
| PM 2 | MDS | 70 | 34.8 | 62.0 | 24.1 | 64.2 | |
| | CD | 20 | 56.4 | 30.6 | 3.7 | 24.7 | |
| | MDL | 10 | 8.7 | 4.6 | 65.6 | 8.6 | |
| PM 3 | MDS | 70 | 54.0 | 26.1 | | | |
| | CD | 20 | 28.6 | | | | |
| | MDL | 10 | 11.5 | 1.0 | | | |
| PM 4 | MDS | 70 | 76.7 | 63.8 | 36.4 | 51.2 | 50.9 |
| | CD | 20 | 17.1 | 28.8 | 45.4 | 34.9 | 41.6 |
| | MDL | 10 | 5.4 | 1.3 | 14.9 | 7.5 | 2.5 |

REDUCING PRODUCT VARIATIONS VIA VARIANCE PARTITION ANALYSIS

TECHNICAL FIELD OF THE INVENTION

Embodiments of the present invention relate to using sensor data to categorize product output variations generated by machine processes as a function of steady state and transient data analysis techniques.

BACKGROUND

Reducing sheet variations on paper machines is desired in the management of paper production processes. Sheet variations increase sheet breaks, reduce product quality, limit machine speed, extend transition times and reduce production. These variations may have their source in bad valves, poor mixing, faulty transmitters, excessive mechanical vibration, or improperly tuned controllers.

Identifying the causes of such problems is generally a time intensive process done after problems are reported. Many diagnostic procedures need to be completed manually by expert level engineers. Further, the value of results from any given manual diagnostic process may be questionable due to the lack of standard analysis techniques, data mining capabilities and technical visualization tools.

BRIEF SUMMARY

In one aspect of the present invention, a method provides automated recognition and categorization of product output variations generated by machine processes as a function of variance partition analysis sensor data. A processing unit determines from variance partition analysis data boxes acquired from scan sensor data for a current reel of paper produced by a paper process machinery system, the following normalized values: an average value of variability of machine direction long-term scan energy over a first time period from an initial time of making two scans of the paper through an end time required to produce the reel of paper; an average value of variability of cross direction profile scan energy observed in a spatial domain over a second time period from an initial time based on a width of two of the data boxes through an end time required to scan a width of the reel of paper; an average value of variability of energy of a remainder of data points that are averaged out from a total of the machine direction long-term scan average energy variability and the cross direction profile scan average energy variability during a third time period time from an initial time of making two data boxes through an end time required to make two scans; and a total variability value as a function of the machine direction long-term scan average energy variability, the cross direction profile scan average energy variability and the data points remainder average energy variability. These determined values are compared to one or more threshold limit values, and an automated diagnosis and analysis function is performed that is specific to a one of the values that exceeds at least one of the threshold limit values.

In another aspect, a system has a processing unit, computer readable memory and a tangible computer-readable storage medium with program instructions. The processing unit, when executing the stored program instructions, determines from variance partition analysis data boxes acquired from scan sensor data for a current reel of paper produced by a paper process machinery system, the following normalized values: an average value of variability of machine direction long-term scan energy over a first time period from an initial time of making two scans of the paper through an end time required to produce the reel of paper; an average value of variability of cross direction profile scan energy observed in a spatial domain over a second time period from an initial time based on a width of two of the data boxes through an end time required to scan a width of the reel of paper; an average value of variability of energy of a remainder of data points that are averaged out from a total of the machine direction long-term scan average energy variability and the cross direction profile scan average energy variability during a third time period time from an initial time of making two data boxes through an end time required to make two scans; and a total variability value as a function of the machine direction long-term scan average energy variability, the cross direction profile scan average energy variability and the data points remainder average energy variability. These determined values are compared to one or more threshold limit values, and an automated diagnosis and analysis function is performed that is specific to a one of the values that exceeds at least one of the threshold limit values.

In another aspect, a computer program product has a tangible computer-readable storage medium with computer readable program code embodied therewith. The computer readable program code comprises instructions that, when executed by a computer processing unit, cause the computer processing unit to determine from variance partition analysis data boxes acquired from scan sensor data for a current reel of paper produced by a paper process machinery system, the following normalized values: an average value of variability of machine direction long-term scan energy over a first time period from an initial time of making two scans of the paper through an end time required to produce the reel of paper; an average value of variability of cross direction profile scan energy observed in a spatial domain over a second time period from an initial time based on a width of two of the data boxes through an end time required to scan a width of the reel of paper; an average value of variability of energy of a remainder of data points that are averaged out from a total of the machine direction long-term scan average energy variability and the cross direction profile scan average energy variability during a third time period time from an initial time of making two data boxes through an end time required to make two scans; and a total variability value as a function of the machine direction long-term scan average energy variability, the cross direction profile scan average energy variability and the data points remainder average energy variability. These determined values are compared to one or more threshold limit values, and an automated diagnosis and analysis function is performed that is specific to a one of the values that exceeds at least one of the threshold limit values.

BRIEF DESCRIPTION OF THE DRAWINGS

These and other features of this invention will be more readily understood from the following detailed description of the various aspects of the invention taken in conjunction with the accompanying drawings in which.

DETAILED DESCRIPTION

Paper machine monitoring and control systems generally output a report at the end of each reel of paper. This data is typically referred to as Variance Partition Analysis (VPA) data. The statistical calculations governing this data vary slightly from user to user. (The term "user" as used herein will be understood to refer generically to automated system user and managers, service providers, vendor or any other entity that may operate or manage paper production processes and machinery.) However, users generally apply their variability measures in such a way as to quantify both machine direction and cross direction variations in the produced sheet of paper.

Figure 1:
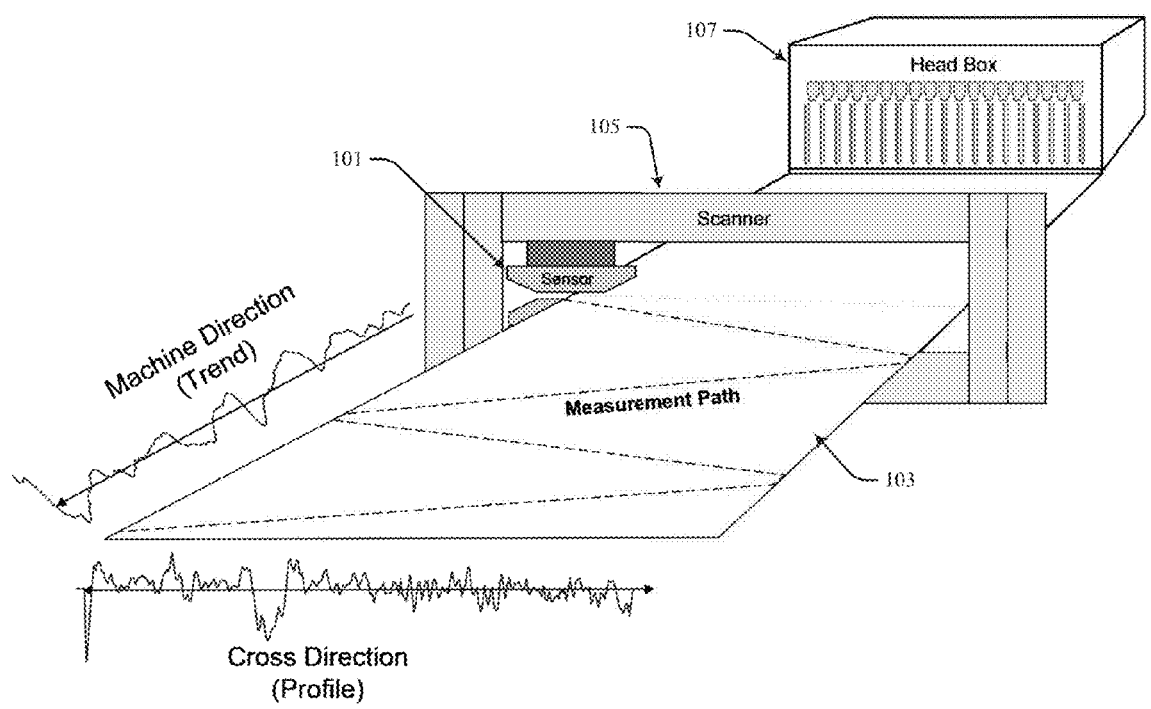
FIG. 1 is a block diagram illustration of a paper production process according to the present invention.

Machine direction variation refers to changes in a paper profile relative to a perspective aligned with movement of a paper sheet as it is produced by the process machinery and conveyed outward onto a roll or other receiving structure or area. Cross direction variation refers to changes in a paper profile relative to a perspective normal to the machine direction, thus along a cross section of the sheet of paper that is itself moving in the machine direction. FIG. 1 illustrates a paper production process. A scanning measurement head 101 records sensor data as the sensor head 101 moves back and forth across a rectangular, planar sheet of paper 103 being produced in a paper production process along a horizontal cross direction that is normal to the machine direction of the movement of the paper sheet 103 as it is conveyed past the scanner housing 105 comprising the sensor 101. As the sensor head 101 moves from one edge of the sheet 103 to the next, sensor data is collected and stored in measurement points commonly referred to as data boxes. Once the sensor 101 has moved from one side of the sheet to the other side of the sheet, the sensor is said to have made one scan across the sheet 103. The data points associated with this scan are commonly referred to as a cross direction single scan profile. A sequence of average profiles is commonly referred to as the scan average trend.

Figure 3:
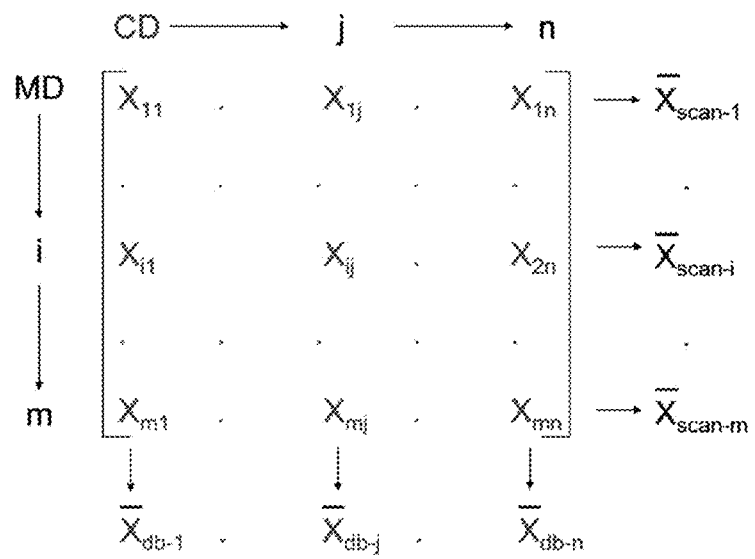
FIG. 3 is a two dimensional matrix or array of scanning measurements according to the present invention.

Embodiments of the present invention may store data associated with scanning measurements in a two dimensional matrix or array, for example as illustrated in FIG. 3 with respect to a horizontal cross direction axis and a vertical machine direction axis, where [n] is the number of data boxes; [j] is a specific data box; [m] is the number of scans in the reel; [i] is a specific scan number; and [x] is a data box point. Statistical equations which may be applied to this array of data are different applications of the variance and standard deviation equations, for example:

$$\text{Var} = \frac{\sum_{n=1}^{N} (\bar{x} - x_n)^2}{N} \quad (1)$$

$$\text{Sigma} = \sqrt{\frac{\sum_{n=1}^{N} (\bar{x} - x_n)^2}{N}} \quad (2)$$

Different users may define these parameters with a variety of terms. For example, a lane may be used to describe a data box and in some cases a scan could represent the sensor package moving from one side of the sheet to the other side and then back again. In any event, the amount of data collected during the creation of a reel of paper can be significant. For example, assuming a scan time of 30 seconds, a reel build time of 60 minutes, and 600 data boxes per scan, the amount of data present for reel report statistics would be approximately 72,000 points per sensor.

One reel of paper may not represent the entire spectral content of paper sheet produced by a given set of paper system control settings. However, examples of the present invention provide a means and process for effectively determining process and control performance from reel VPA by quantifying the relative values of machine direction and cross direction reel report data in a novel approach useful in troubleshooting, benchmarking, and comparison purposes.

Figure 2:
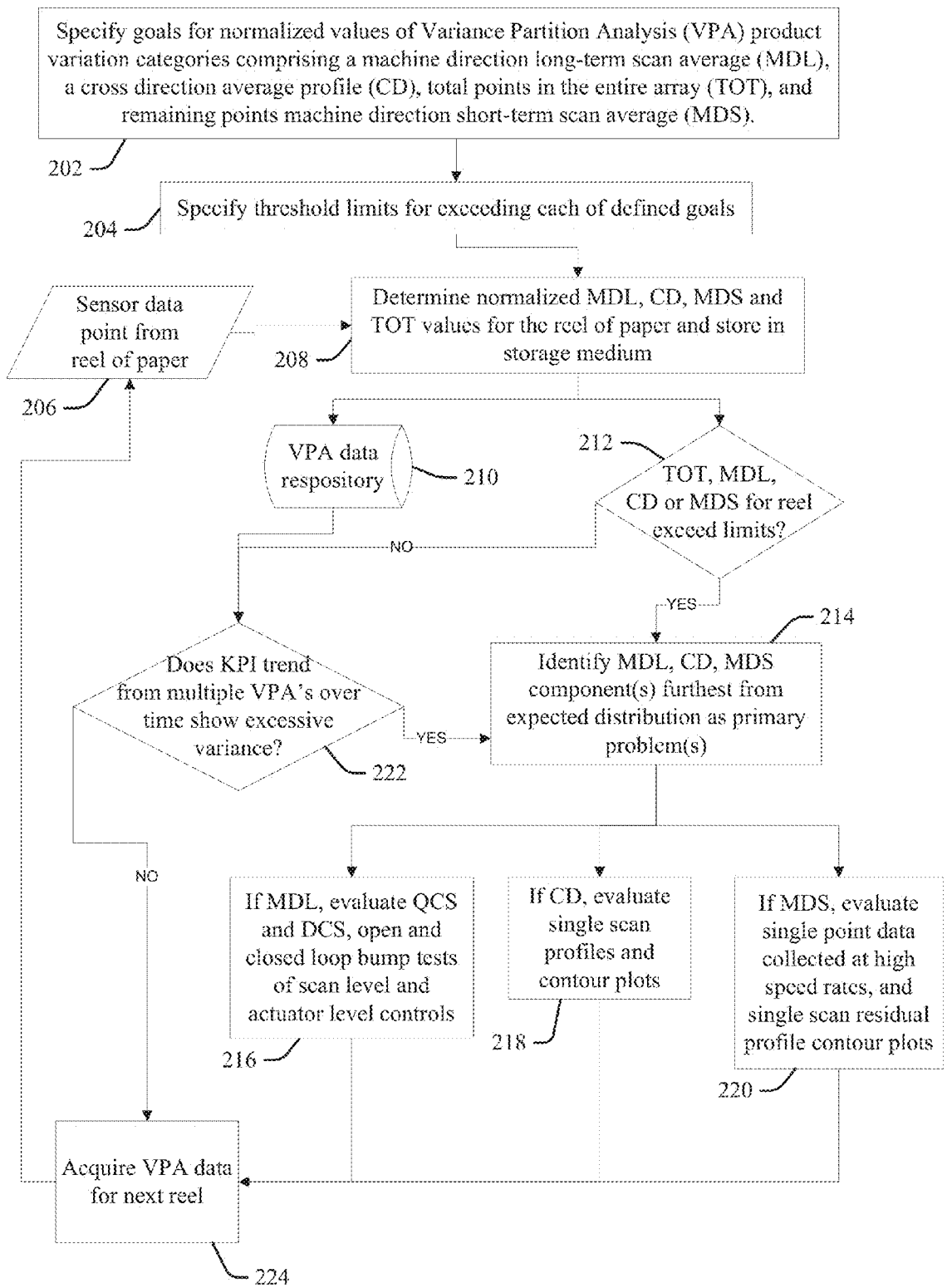
FIG. 2 is a block diagram illustration of a process or system for automated recognition and categorization of product output variations generated by machine processes as a function of sensor data according to the present invention.

More particularly, FIG. 2 illustrates a process or system for automated recognition and categorization of product output variations generated by machine processes as a function of VPA sensor data according to the present invention. At 202 goals are defined for an acceptable total variability (TOT) of Variance Partition Analysis (VPA) data for data inputs from process machinery sensors as a percent of process, and for the relative normalized values each of a plurality of VPA data categories. The VPA data categorizes product variation via statistical analysis of collected data points, and the component categories includes a machine direction long-term scan average (MDL) and a cross direction average profile (CD). The entire array of the VPA data for the reel defines a total (TOT) amount of data points and also include remaining points once the average profile (MDL) and scan average trend (CD) have been removed, which is referred to as the machine direction short-term scan average (MDS) or "Residual."

The machine direction long-term scan average value (MDL) is a long-term trend variability in the scan average for a single reel of paper, and assumes a sufficient number of scans made in a reel to generate a meaningful trend; this generally represents energy observed over the period of time from an initial time of making two scans of the paper through an end time required to produce the reel of paper.

The cross direction average profile value (CD) is equivalent to the variability in the average reel profile and (assuming a sufficient number of scans in a reel to get meaningful data) represents the energy observed in the spatial domain over the period of time from an initial time based on the width of two data boxes through an end time required to scan the width of a reel.

The remainder data points are termed the short term or residual variability (MDS) and represent the residual variations that get averaged out in the scan average and profile average during a reel; this is the energy observed over the period of time from an initial time of making two data boxes through an end time required to make two scans.

The total variability (TOT) is not the only indicator of product problems. The distribution of the components that make up the total variability is also important. Since the variance sum of MDL, CD, and MDS has to equal the total TOT, this implies that as a percentage of the total, the sum of MDL, CD and MDS should add up to 100 percent. In order to calculate the distribution, embodiments of the present invention convert the sigma values to variance, and then the variance of MDL, CD, and MDS is converted into a percentage of the total variance.

More particularly, the total variability TOT is a value that represents the variability of each data box in an entire reel. Aspects of the present invention define the relation of the MDL, CD and MDS values to each other as a function of the total variability TOT pursuant to the following (assuming two sigma-based VPA data):

$$TOT = 2 \times \sqrt{\left(\frac{MDS}{2}\right)^2 + \left(\frac{MDL}{2}\right)^2 + \left(\frac{CD}{2}\right)^2} \quad (3)$$

Figure 4:
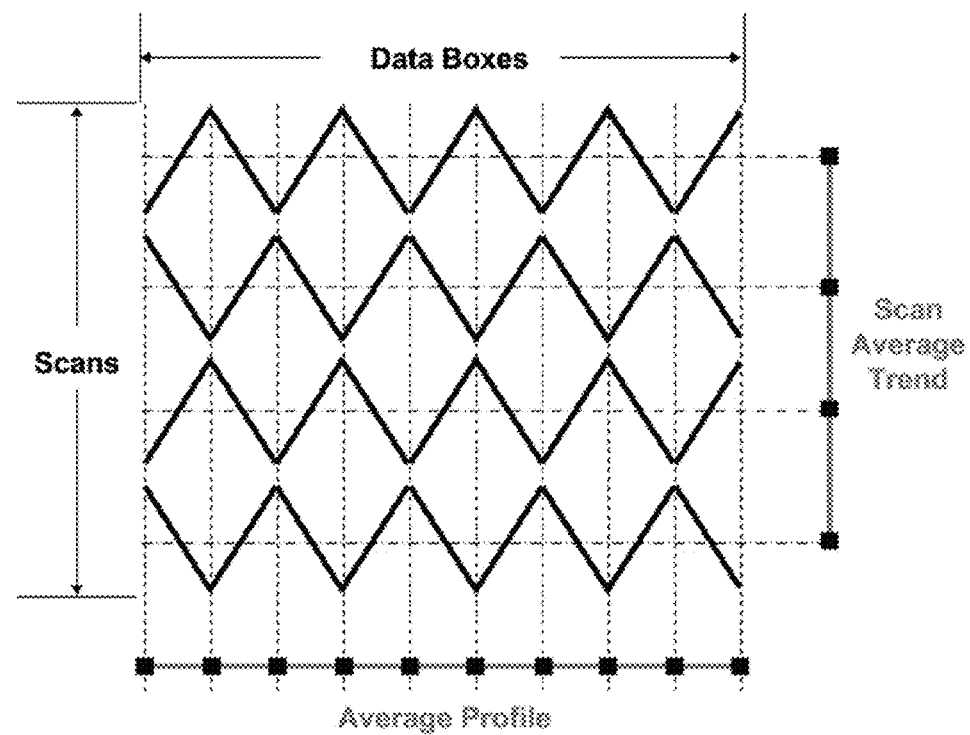
FIG. 4 is a graphical illustration of a relationship between the variability areas in successive scans according to the present invention.

The relationship between the variability areas can be seen in the example illustrated in FIG. 4, wherein each successive scan is an exact minor image of the previous scan, the scan values essentially flip-flopping from scan to scan. It is apparent that this flip-flop action may result in both the average profile and scan average trending to have no overall variability over scan multiples, with consecutive scans essentially cancelling each other out. However, the total variability actually present in the reel is considerable. Embodiments of the present invention recognize total variability values in this example by considering the residual or short term variability component of the process. If the residual component is not being calculated or otherwise considered as part of the total variability value, then the source of this variability could go undetected.

Accordingly, embodiments of the present invention consider the relative frequency content of each of the MDL, CD and MDS attribute components in defining the total variability TOT when analyzing the VPA data. Such embodiments define VPA frequency content as a function of one or more of the following factors: scan time, trim width, number of data boxes, data box width, data box build time, reel build time, and sensor type; and still others may be considered.

Aspects of the present invention couple VPA frequency bands with process information to identify machine direction variability sources. Consider one example of VPA data from two different machines in a paper production process or system, wherein VPA data is obtained from a first ("Machine A") with respect to a 30 second scan time, 600 data boxes, a reel build time of 60 minutes, and a trim width of 200 inches; and VPA data is obtained from the second ("Machine B") with respect to a 60 second scan time, 60 data boxes, a reel build time of 60 minutes, and a trim width of 200 inches. Machine A accordingly has the following variability frequency band: CD is 0.67 inch/cycle to 200 inches per cycle; MDS is 10 Hz to 60 seconds; and MDL is 60 seconds to 60 minutes. In contrast, Machine B has the following variability frequency band: CD is 6.7 inch/cycle to 200 inches; MDS is 0.5 Hz to 2 minutes; and MDL is 120 minutes to 60 minutes.

Figures 5, 6:
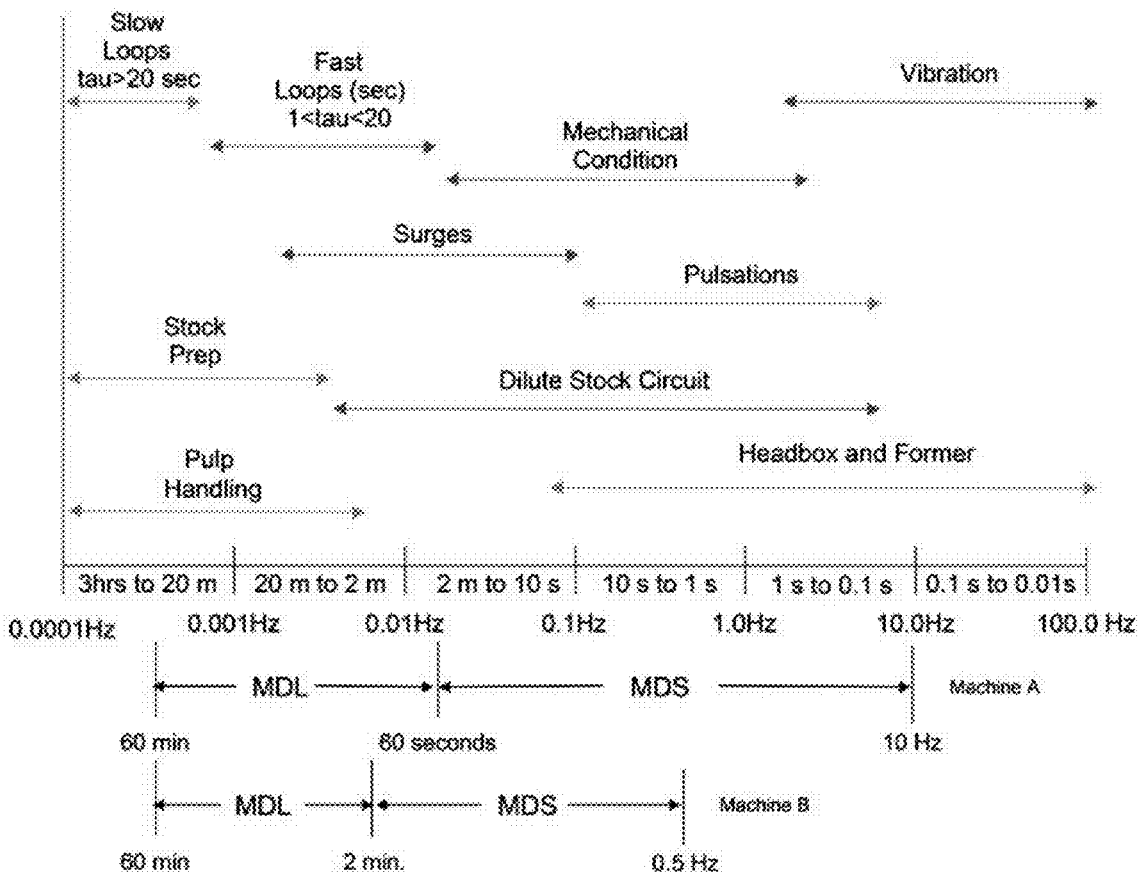
FIG. 5 is a graphical illustration of a frequency map chart showing common variability sources with respect to two process machines according to the present invention.
FIG. 6 is a graphical illustration of a table of variability values for machine sensors according to the present invention.

FIG. 5 is a frequency map chart that shows common variability sources with respect to the Machine A and Machine B data, and the frequency bands with which they are associated. It is apparent that the number of data boxes and scan time impact the frequency ranges associated with different MDL and MDS values for Machine A and Machine B. This difference makes directly comparing the data outputs of these two machines from a prior art VPA perspective difficult, if not impossible.

Moreover, quantifying and comparing VPA data from different machines, or even for different paper grades on the same machine can be challenging when using absolute variability numbers, as is common in the prior art. For example, a total variability number of two pounds (lbs.) means very different things if the average weight is 20 lbs. or 200 lbs. Accordingly, embodiments of the present invention determine the total variability (TOT) and the MDS, CD and MDL values as "percent of process" values. This takes advantage of the fact that VPA data is statistical by nature and is generally a function of the DC or average component of the process.

Embodiments of the present invention thus define the goals at 202 (FIG. 2) by normalizing the determination and comparison of average value data, for example pursuant to:

$$\% \text{ of Process} = 100 \text{Total}/\text{ProcessAverage}. \quad (4)$$

In one example the following rules of thumb are used as goals at 202 to quantify relative process variability for a total value (100%) of TOT: MDS of 70%, CD of 20%, and MDL of 10%. Other embodiments may use other values, and this example is not limiting upon the invention embodiments disclosed herein. The goals are not absolutes, but rather indicators of product variability distribution problems: compliance with these standards is desired, but failure to comply with the goals alone may not generally trigger alerts or call for process component adjustments, or other automatic attention.

At 204 of FIG. 2 threshold limits are defined for exceeding the values of each of the defined MDL, CD, MDS goals, wherein the MDL, CD, MDS relative value that exceeds a given limit triggers an automated analysis and diagnosis of problematic component settings associated with the specific MDL, CD, MDS value. The goals and limits defined at 202 and 204 may comprise overall, system goals and limits, as well as machine, sensor or component-specific goals and limits. The goals defined at 202 are targets for achievement in the operation of a paper machine process, while the limits defined at 204 are the boundaries which, if violated, prompt an automated VPA Analyzer to recognize that there is a problem, and in some implementations to perform automated diagnosis and analysis functions specific to the one of the MDL, CD, MDS values exceeding its limit. In one example for the VPA goals of MDS 70%, CD 20%, and MDL 10%, threshold limits are defined at 204 as MDS 75%, CD 25%, and MDL 15%, though different values may be practiced in other embodiments.

Accordingly, in response to receiving sensor input for a reel of paper 206, at 208 the present embodiment determines normalized values of total variability (TOT) of the data boxes for the entire reel, as well as the relative MDL, CD, and MDS component values of the total variability (TOT) for the reel, and stores the determined values in a VPA data repository 210 (for example, within a database located on a server, on a non-volatile memory device, a generic tangible computer-readable storage medium, etc.).

At 212 the total variability (TOT) and the relative MDL, CD, and MDS component values for the reel are compared to their respective limits or thresholds. If any one of the TOT, MDL, CD, and MDS values exceed their limits or thresholds, then the relative values of the MDL, CD, and MDS components are compared to their respective limits (defined at 204) at 214, and the MDL, CD or MDS component or components that exceed their respective limits are identified. The appropriate diagnostic or corrective procedure is then selected and executed at 216, 218 or 220.

More particularly, excessive variability in the MDL region exceeding the limit defined at 204 for this value typically indicates a problem with the scan level weight and moisture controls, additive or pulping cycles, or low frequency problems coming from the stock or steam approach systems. In one embodiment of the present invention this indicates or requires evaluation at 216 of Quality Control System (QCS) and Distributed Control System (DCS) data, and open and closed loop bump tests of scan level and actuator level controls.

Excessive variability in the CD area (exceeding the limit at 214 that is defined at 204 for this value) may indicate cross direction actuators being out of range, the head box 107 (FIG. 1) not operating within design specification or having consistency problems, cross direction controls are not properly set up for the grade of paper of the reel, dirty wires, or felt problems. Diagnosis at 218 accordingly generally requires evaluation of single scan profiles and contour plots.

Excessive variability in the MDS region (exceeding the limit at 214 that is defined at 204 for this value) generally indicates problems in mixing, cleaners, machine clothing, and possibly poor actuator level regulatory control. Diagnosis at 220 generally requires evaluation of single point data collected at high rates of speed, as well as evaluation of single scan residual profile contour plots.

Embodiments of the present invention also provide for analysis and insights into tendencies of the machine process to either improve or get worse from reel to reel, and may thereby take diagnostic action even when current VPA data is within tolerances and limits. More particularly, the present example also determines VPA value trends over time by evaluating long term impacts of product variability at 222 for the VPA data of a plurality of reels stored in the repository 210. Thus, VPA data for a period time comprising a plurality of reels including the most recent reel data 206 is retrieved at 222 from the VPA repository 210 and Key Performance Indicators (KPI) trends for the normalized MDL, CD, MDS and TOT values are determined. The paper product attributes determined from sensor data may not have exceeded allowable limits yet, but if the trend of variability is going up it probably will exceed the limits: embodiments of the invention enable taking action now, in advance of the paper product actually violating limits. Accordingly, if any of the determined trends shows excessive variance or some other trend of concern that exceeds an associated limit or threshold as defined and applied at 222, then the automated MDL, CD and MDS identification and diagnosis processes of 214-216-218-220 are triggered. The process of FIG. 2 repeats at 224 with acquisition of each new batch of VPA data from subsequent reels of paper.

Trending KPI's are calculated at 222 over multiple reels rather than just one reel of data, in some applications on a periodic basis. In one example a KPI analysis is performed once a week at 222 with respect to a trailing, previous three months of VPA data, and thus the KPI trend determined for any given week is based on a three-month overlap of data. This enables the process to respond to negative trends and take action even where VPA for the current reel is still within limits.

The limits applied to the single reel of VPA data at 212 are also applied to a longer KPI trend for these same components at 222 in a KPI "percent of process limit rule." If the total variability TOT, or any of the relative distribution values MDL, CD or MDS values are trending upward in a progression that will take them beyond their limits in a future extrapolation at 222, then the appropriate diagnostic process may be triggered now at 214-216-218-220, rather than waiting for some later reel KPA data to itself provide the VPA data necessary to trigger intervention.

KPI trend determination at 222 may also include considering the total variability normalized as part of the process value in a "best fit line slope rule" analysis. If the "best fit" for a slope of a determined trend line is greater than one, this indicates that there is an increasing amount of variability and that associated sensor data is in violation of acceptable performance requirements.

KPI trend determination at 222 may also include application of a "sigma rule," to determine if a trending standard deviation is greater than a threshold value percentage of the mean, for example 5%. This recognizes that even if the variable distributions are fine, and are not increasing too quickly, intervention may be triggered if VPA values are oscillating or bouncing around a lot, more than a specified threshold.

FIGS. 6 through 9 illustrate one example of a VPA analysis according to the embodiment depicted in FIG. 2 with respect to four paper machines ("PM") PM1, PM2, PM3 and PM4 within a paper production process line. Each of the machines have the sensors listed in the columns shown in the table of FIG. 6, with respect goals or limits for values of each of the sensors: Conditioned Weight <1.5%; Moisture <10%; Caliper <1%; and Ash <4%. The values in the table entries for each of the machines in FIG. 6 represent the total variability for each of respective machine sensors. While several of the values are higher than expected (over their respective goals as specified in each column), two areas are over double what is expected: the PM3 moisture value of 23.2, and the PM1 size moisture value of 25.1, and each thereby indicate that there is much more variability than is to be expected relative to the other machine values. The analysis thus far only shows that there is a problem, but does not provide insight into where that problem might be.

Figures 7, 8:
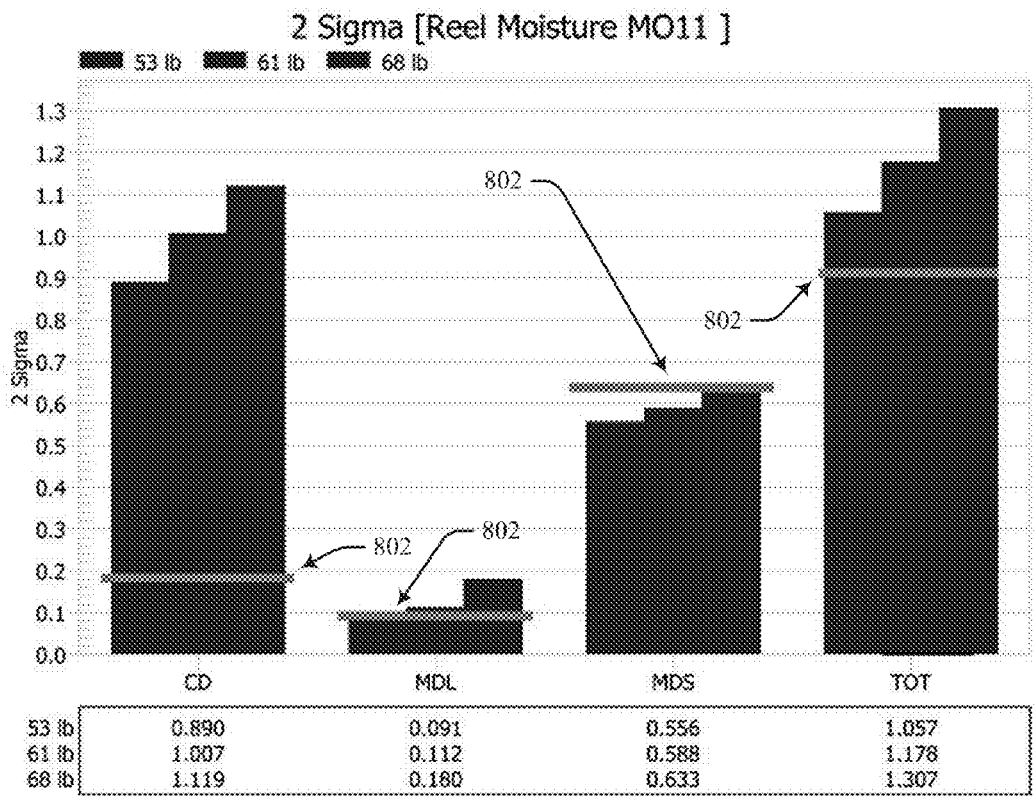
FIG. 7 is a graphical illustration of a table of variability value components for the variability values of FIG. 6.
FIG. 8 is a bar graph illustration of machinery variability and variance distribution values according to the present invention.

The table in FIG. 7 shows the distribution of the TOT energy for each of these machines as broken down into their MDS, CD and MDL components. Review of this data shows that the variance distribution on machine PM3 for moisture (MDS-26.1, CD-72.2 and MDL-1.0) is not close to the expected distribution (MDS-70, CD-20 and MDL-10). This indicates that a primary problem is with the cross direction component of the variability. In this example the paper machines PM3 and PM4 make overlapping paper grades, and the reason that the CD component is so much worse on PM3 than on PM4 is because PM3 does not have a cross direction actuator for moisture, while PM4 does. The raw data associated with each machine is presented by the bar graph of FIG. 8, wherein the horizontal bars 802 each represent the respective goals based on total variability and ideal variance distributions.

Figure 9:
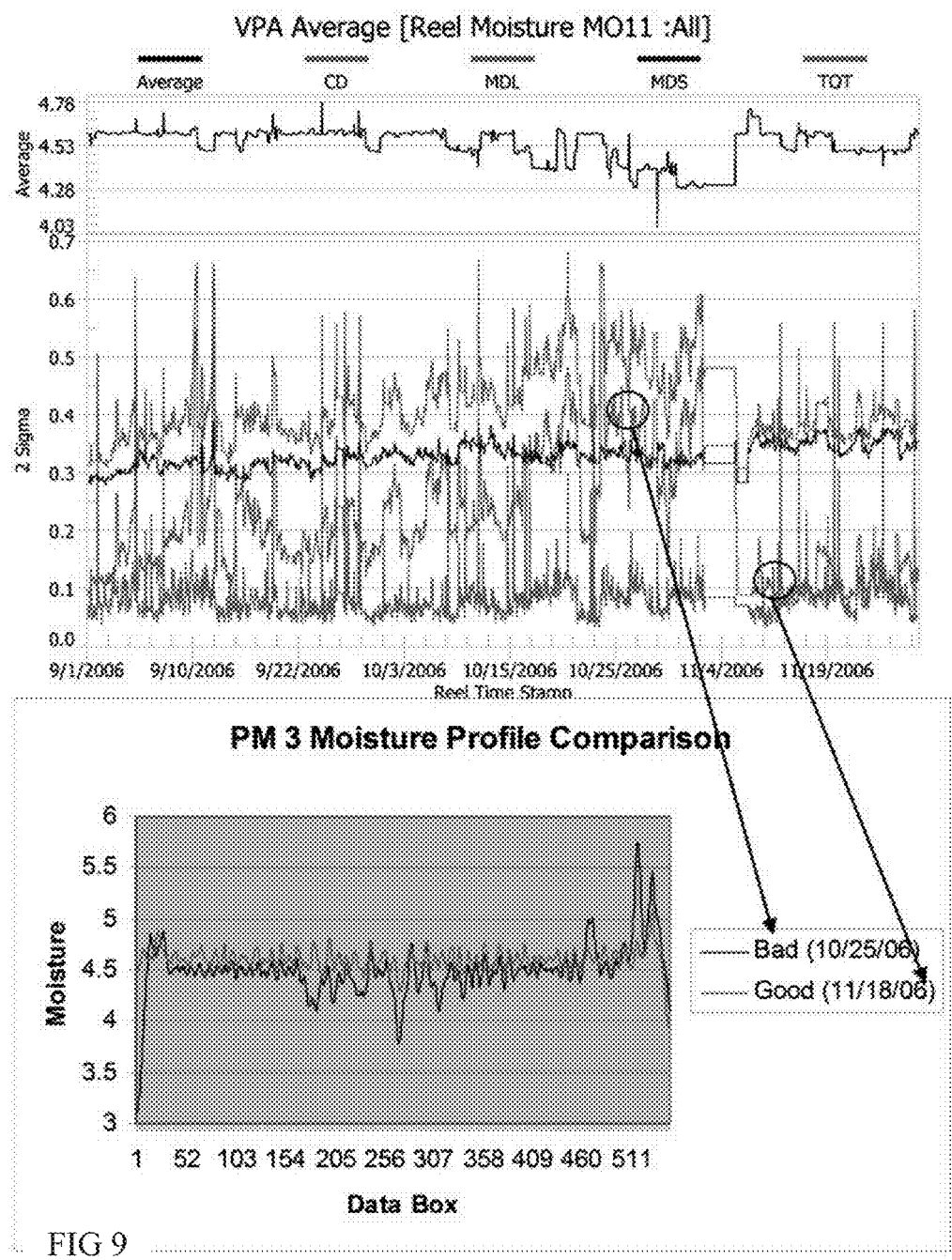
FIG. 9 is a graphical illustration of variability data varied over time determined with respect to Key Performance Indicators according to the present invention.

FIGS. 6 through 8 represent data from a single reel and may be described as a static snapshot of VPA analysis. This type of analysis is powerful, but as it is limited to a single reel of data it cannot provide insights into tendencies of the performance of the paper production machinery to improve or get worse over time relative to other reels of produced paper. In order to evaluate the long term impact of product variability, VPA trending is by embodiments of the present invention. FIG. 9 illustrates a three month period of VPA variability data extracted from a mills data historian (for example, from the repository 210 of FIG. 2) wherein outliers are removed.

Review of data in FIG. 9 shows that the CD variability component gradually increased from Sep. 1, 2006 through Nov. 14, 2006, and embodiments of the present invention may determine or recognize this increasing trend at 222 and 214 of FIG. 2. In one example this observed trend indicates a problem related to the head box 107 of FIG. 1, which may be diagnosed via the automated diagnostic process at 218. Upon correction of the head box problem, the subsequent CD component value (on and after Nov. 18, 2006) improves by over 50%. The VPA data clearly shows the decline in performance and the subsequent improvement in performance. The profile data associated with the VPA data just before and after the repair visually match the CD component being trended. Earlier recognition of the trend via the processes of FIG. 2 may also detect and solved the problem earlier, in some examples as much as four weeks earlier.

Figure 10:
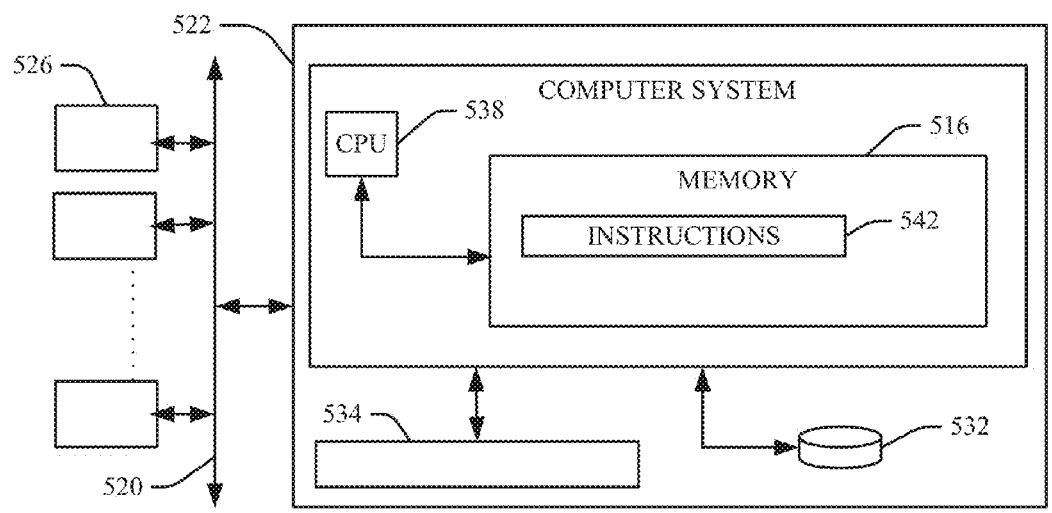
FIG. 10 is a block diagram illustration of a computerized implementation of a system and method according to the present invention.

Referring now to FIG. 10, an exemplary computerized implementation of an embodiment of the present invention includes a computer system or other programmable device 522 in communication with a plurality of process sensor data sources 526 (such as the sensor 101 of FIG. 1 providing real-time data, the VPA data repository 210 of FIG. 2, or other data sources). Instructions 542 reside within computer readable code in a computer readable memory 534, or in a computer readable storage system 532, or other tangible computer readable storage medium that is accessed through a computer network infrastructure 520 by a processing unit (CPU) 538. Thus, the instructions, when implemented by the processing unit (CPU) 538, cause the processing unit (CPU) 538 to provide automated recognition and categorization of product output variations generated by machine processes as a function of VPA sensor data as described above with respect to FIG. 2.

Embodiments of the present invention may also perform process steps of the invention on a subscription, advertising, and/or fee basis. That is, a service provider could offer to integrate computer-readable program code into the computer system 522 to enable the computer system 522 to provide automated recognition and categorization of product output variations generated by machine processes as a function of VPA sensor data as described above with respect to FIG. 2. The service provider can create, maintain, and support, etc., a computer infrastructure such as the computer system 522, network environment 520, or parts thereof, that perform the process steps of the invention for one or more customers. In return, the service provider can receive payment from the customer(s) under a subscription and/or fee agreement. Services may comprise one or more of: (1) installing program code on a computing device, such as the computer device 522, from a tangible computer-readable medium device 534 or 532; (2) adding one or more computing devices to a computer infrastructure; and (3) incorporating and/or modifying one or more existing systems of the computer infrastructure to enable the computer infrastructure to perform the process steps of the invention.

The terminology used herein is for describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof. Certain examples and elements described in the present specification, including in the claims and as illustrated in the Figures, may be distinguished or otherwise identified from others by unique adjectives (e.g., a "first" element distinguished from another "second" or "third" of a plurality of elements, a "primary" distinguished from a "secondary" one or "another" item, etc.) Such identifying adjectives are generally used to reduce confusion or uncertainty, and are not to be construed to limit the claims to any specific illustrated element or embodiment, or to imply any precedence, ordering or ranking of any claim elements, limitations or process steps.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in a baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A system for providing automated recognition and categorization of product output variations generated by machine processes as a function of variance partition analysis sensor data, the system comprising:

a processing unit in communication with a computer-readable memory and a tangible computer-readable storage medium;

wherein the processing unit, in response to executing program instructions stored on the tangible computer-readable storage medium via the computer readable memory:

determines from a plurality of variance partition analysis data boxes acquired from scan sensor data for a current reel of paper produced by a paper process machinery system, and stores in a variance partition analysis data repository, normalized values of:

an average value of variability of machine direction long-term scan energy over a first time period from an initial time of making two scans of the paper through an end time required to produce the reel of paper (MDL);

an average value of variability of cross direction profile scan energy observed in a spatial domain over a second time period from an initial time based on a width of two of the data boxes through an end time required to scan a width of the reel of paper (CD); and an average value of variability of energy of a remainder of data points that are averaged out from a total of the machine direction long-term scan average energy variability and the cross direction profile scan average energy variability during a third time period time from an initial time of making two data boxes through an end time required to make two scans (MDS);

determines a total variability value (TOT) as equal to:

$$\left[ 2 \times \sqrt{ \left(\frac{MDS}{2}\right)^2 + \left(\frac{MDL}{2}\right)^2 + \left(\frac{CD}{2}\right)^2 } \right];$$

determines an MDL percentage as a percentage that the MDL is of the TOT, a CD percentage as a percentage that the CD is of the TOT, and an MDS percentage as a percentage that the MDS is of the TOT;

compares the MDL percentage to an MDL threshold limit value, the CD percentage to a CD threshold limit value, and the MDS percentage to an MDS threshold limit value; and performs an automated diagnosis and analysis function that is specific to the machine direction long-term scan average energy variability determined for the reel of paper in response to the MDL percentage exceeding the MDL threshold limit value, that is specific to the cross direction profile scan average energy variability determined for the reel of paper in response to the CD percentage exceeding the CD threshold limit value, or that is specific to the data points remainder average energy variability determined for the reel of paper in response to the MDS percentage exceeding the MDS threshold limit value.

2. The system of claim 1, wherein the processing unit, in response to executing the program instructions stored on the tangible computer-readable storage medium via the computer readable memory, further:
   determines a trend value that represents a change in value over time of a plurality of the values for the total variability value, the machine direction long-term scan average energy variability, the cross direction profile scan average energy variability or the data points remainder average energy variability that are each stored in the variance partition analysis data repository with respect to variance partition analysis data for each of a plurality of different paper reels and that are acquired consecutively over a trend period of time;
   compares the trend value determined for the plurality of reels of paper to a threshold limit of the at least one threshold limit value; and
   performs the automated diagnosis and analysis function specific to a one of machine direction long-term scan average energy variability, cross direction profile scan average energy variability and data points remainder average energy variability components of the trend value that is determined for the plurality of reels of paper and that exceeds the at least one threshold limit value.

3. The system of claim 2, wherein the processing unit, in response to executing the program instructions stored on the tangible computer-readable storage medium via the computer readable memory, performs the automated diagnosis and analysis function that is specific to either of the machine direction long-term scan average energy variability determined for the reel of paper or the trend value machine direction long-term scan average energy variability component determined for the plurality of reels of paper exceeding the at least one threshold limit value, by evaluating quality control system data, distributed control system data, open and closed loop bump tests of scan level, and actuator level controls.

4. The system of claim 2, wherein the processing unit, in response to executing the program instructions stored on the tangible computer-readable storage medium via the computer readable memory, performs the automated diagnosis and analysis function that is specific to either of the cross direction profile scan average energy variability determined for the reel of paper or the trend value cross direction profile scan average energy variability component determined for the plurality of reels of paper exceeding the at least one threshold limit value, by evaluating single scan profiles and contour plots.

5. The system of claim 2, wherein the processing unit, in response to executing the program instructions stored on the tangible computer-readable storage medium via the computer readable memory, performs the automated diagnosis and analysis function that is specific to either of the data points remainder average energy variability determined for the reel of paper or the trend value data points remainder average energy variability component determined for the plurality of reels of paper exceeding the at least one threshold limit value, by evaluating single point data collected at high rates of speed, and single scan residual profile contour plots.

6. The system of claim 2, wherein the processing unit, in response to executing the program instructions stored on the tangible computer-readable storage medium via the computer readable memory, determines that the trend value that is determined for the plurality of reels of paper exceeds the at least one threshold limit value if a slope of a trend line over time for the determined trend value is greater than one.

7. The system of claim 2, wherein the processing unit, in response to executing the program instructions stored on the tangible computer-readable storage medium via the computer readable memory, determines that the trend value that is determined for the plurality of reels of paper exceeds the at least one threshold limit value if a trending standard deviation over time for the determined trend value is greater than a threshold value percentage of the mean.

8. A method for providing automated recognition and categorization of product output variations generated by machine processes as a function of variance partition analysis sensor data, the method comprising:
   determining from a plurality of variance partition analysis data boxes acquired from scan sensor data for a current reel of paper produced by a paper process machinery system, and stores in a variance partition analysis data repository, normalized values of:
      an average value of variability of machine direction long-term scan energy over a first time period from an initial time of making two scans of the paper through an end time required to produce the reel of paper (MDL);
      an average value of variability of cross direction profile scan energy observed in a spatial domain over a second time period from an initial time based on a width of two of the data boxes through an end time required to scan a width of the reel of paper (CD); and
      an average value of variability of energy of a remainder of data points that are averaged out from a total of the machine direction long-term scan average energy variability and the cross direction profile scan average energy variability during a third time period time from an initial time of making two data boxes through an end time required to make two scans (MDS);
   determining a total variability value (TOT) as equal to:

$$\left[ 2 \times \sqrt{\left(\frac{MDS}{2}\right)^2 + \left(\frac{MDL}{2}\right)^2 + \left(\frac{CD}{2}\right)^2} \right];$$

comparing the total variability value determined for the reel of paper, the machine direction long-term scan average energy variability determined for the reel of paper, the cross direction profile scan average energy variability determined for the reel of paper, and the data points remainder average energy variability determined for the reel of paper to at least one threshold limit value;
   determining an MDL percentage as a percentage that the MDL is of the TOT, a CD percentage as a percentage that the CD is of the TOT and an MDS percentage as a percentage that the MDS is of the TOT; and
   executing an automated diagnosis and analysis function on a processing unit, wherein the automated diagnosis and analysis function is specific to the machine direction long-term scan average energy variability determined for the reel of paper in response to the MDL percentage exceeding the MDL threshold limit value, is specific to the cross direction profile scan average energy variability determined for the reel of paper in response to the CD percentage exceeding the CD threshold limit value, or is specific to the data points remainder average energy variability determined for the reel of paper in response to the MDS percentage exceeding the MDS threshold limit value.

9. The method of claim 8, further comprising:
determining a trend value that represents a change in value over time of a plurality of the values for the total variability value, the machine direction long-term scan average energy variability, the cross direction profile scan average energy variability or the data points remainder average energy variability that are each stored in the variance partition analysis data repository with respect to variance partition analysis data for each of a plurality of different paper reels and that are acquired consecutively over a trend period of time;
comparing the trend value determined for the plurality of reels of paper to a threshold limit of the at least one threshold limit value; and
wherein the automated diagnosis and analysis function is specific to one of machine direction long-term scan average energy variability, cross direction profile scan average energy variability and data points remainder average energy variability components of the trend value that is determined for the plurality of reels of paper and that exceeds the at least one threshold limit value.

10. The method of claim 9, wherein the automated diagnosis and analysis function is specific to either of the machine direction long-term scan average energy variability determined for the reel of paper or the trend value machine direction long-term scan average energy variability component determined for the plurality of reels of paper exceeding the at least one threshold limit value; and
the step of executing the automated diagnosis and analysis function on the processing unit further comprises evaluating quality control system data, distributed control system data, open and closed loop bump tests of scan level, and actuator level controls.

11. The method of claim 9, wherein the automated diagnosis and analysis function is specific to either of the cross direction profile scan average energy variability determined for the reel of paper or the trend value cross direction profile scan average energy variability component determined for the plurality of reels of paper exceeding the at least one threshold limit value; and
the step of executing the automated diagnosis and analysis function on the processing unit further comprises evaluating single scan profiles and contour plots.

12. The method of claim 9, wherein the automated diagnosis and analysis function is specific to either of the data points remainder average energy variability determined for the reel of paper or the trend value data points remainder average energy variability component determined for the plurality of reels of paper exceeding the at least one threshold limit value; and
the step of executing the automated diagnosis and analysis function on the processing unit further comprises evaluating single point data collected at high rates of speed, and single scan residual profile contour plots.

13. The method of claim 9, further comprising:
determining that the trend value that is determined for the plurality of reels of paper exceeds the at least one threshold limit value if a slope of a trend line over time for the determined trend value is greater than one.

14. The method of claim 9, further comprising:
determining that the trend value that is determined for the plurality of reels of paper exceeds the at least one threshold limit value if a trending standard deviation over time for the determined trend value is greater than a threshold value percentage of the mean.

15. The method of claim 9, further comprising:
integrating computer-readable program code into a computer system comprising a processing unit, a computer readable memory and a computer readable tangible storage medium, wherein the computer readable program code is embodied on the computer readable tangible storage medium and comprises instructions that cause the processing unit, in response to executing the instructions via the computer readable memory, to perform the steps of determining the normalized values of the average value of variability of machine direction long-term scan energy, the average value of variability of cross direction profile scan energy observed in the spatial domain, the average value of variability of energy of the remainder of data points and the total variability value;
determining the MDL percentage and the CD percentage and the MDS percentage, comparing the MDL percentage to the MDL threshold limit value and the CD percentage to the CD threshold limit value and the MDS percentage to the MDS threshold limit value; and
executing the automated diagnosis and analysis function.

16. A computer program product for providing automated recognition and categorization of product output variations generated by machine processes as a function of variance partition analysis sensor data, the computer program product comprising:
a computer readable tangible storage medium having computer readable program code embodied therewith, the computer readable program code comprising instructions that cause a computer processing unit, in response to executing the instructions via a computer readable memory, to:
determine from a plurality of variance partition analysis data boxes acquired from scan sensor data for a current reel of paper produced by a paper process machinery system, and stores in a variance partition analysis data repository, normalized values of:
an average value of variability of machine direction long-term scan energy over a first time period from an initial time of making two scans of the paper through an end time required to produce the reel of paper (MDL);
an average value of variability of cross direction profile scan energy observed in a spatial domain over a second time period from an initial time based on a width of two of the data boxes through an end time required to scan a width of the reel of paper (CD); and
an average value of variability of energy of a remainder of data points that are averaged out from a total of the machine direction long-term scan average energy variability and the cross direction profile scan average energy variability during a third time period time from an initial time of making two data boxes through an end time required to make two scans (MDS);
determine a total variability value (TOT) as equal to:

$$\left[ 2 \times \sqrt{\left(\frac{MDS}{2}\right)^2 + \left(\frac{MDL}{2}\right)^2 + \left(\frac{CD}{2}\right)^2} \right];$$

determine an MDL percentage as a percentage that the MDL is of the TOT, a CD percentage as a percentage that the CD is of the TOT, and an MDS percentage as a percentage that the MDS is of the TOT;

compare the MDL percentage to an MDL threshold limit value, the CD percentage to a CD threshold limit value, and the MDS percentage to an MDS threshold limit value; and perform an automated diagnosis and analysis function that is specific to the machine direction long-term scan average energy variability determined for the reel of paper in response to the MDL percentage exceeding the MDL threshold limit value, that is specific to the cross direction profile scan average energy variability determined for the reel of paper in response to the CD percentage exceeding the CD threshold limit value, or that is specific to the data points remainder average energy variability determined for the reel of paper in response to the MDS percentage exceeding the MDS threshold limit value.

17. The computer program product of claim 16, wherein the computer readable program code instructions further cause the computer processing unit, in response to executing the instructions via the computer readable memory, to:

determine a trend value that represents a change in value over time of a plurality of the values for the total variability value, the machine direction long-term scan average energy variability, the cross direction profile scan average energy variability or the data points remainder average energy variability that are each stored in the variance partition analysis data repository with respect to variance partition analysis data for each of a plurality of different paper reels and that are acquired consecutively over a trend period of time;

compare the trend value determined for the plurality of reels of paper to a threshold limit of the at least one threshold limit value; and perform the automated diagnosis and analysis function specific to a one of machine direction long-term scan average energy variability, cross direction profile scan average energy variability and data points remainder average energy variability components of the trend value that is determined for the plurality of reels of paper and that exceeds the at least one threshold limit value.

18. The computer program product of claim 16, wherein the computer readable program code instructions further cause the computer processing unit, in response to executing the instructions via the computer readable memory, to perform the automated diagnosis and analysis function by evaluating quality control system data, distributed control system data, open and closed loop bump tests of scan level, and actuator level controls.

19. The computer program product of claim 16, wherein the computer readable program code instructions further cause the computer processing unit, in response to executing the instructions via the computer readable memory, to perform the automated diagnosis and analysis function by evaluating single scan profiles and contour plots.

20. The computer program product of claim 16, wherein the computer readable program code instructions further cause the computer processing unit, in response to executing the instructions via the computer readable memory, to perform the automated diagnosis and analysis function by evaluating single point data collected at high rates of speed, and single scan residual profile contour plots.

* * * * *